United States Patent
Liu et al.

(10) Patent No.: US 8,536,695 B2
(45) Date of Patent: Sep. 17, 2013

(54) CHIP-LAST EMBEDDED INTERCONNECT STRUCTURES

(75) Inventors: Fuhan Liu, Atlanta, GA (US); Nitesh Kumbhat, Atlanta, GA (US); Venkatesh Sundaram, Alpharetta, GA (US); Rao R. Tummala, Greensboro, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 35 days.

(21) Appl. No.: 13/415,503

(22) Filed: Mar. 8, 2012

(65) Prior Publication Data

US 2012/0228754 A1 Sep. 13, 2012

Related U.S. Application Data

(60) Provisional application No. 61/450,432, filed on Mar. 8, 2011.

(51) Int. Cl.
*H01L 23/12* (2006.01)
*H01L 21/4763* (2006.01)
*H05K 1/00* (2006.01)
*H05K 1/03* (2006.01)

(52) U.S. Cl.
USPC .... 257/700; 257/758; 257/774; 257/E23.041; 257/E23.145; 361/748; 174/255; 174/262; 438/637; 438/667

(58) Field of Classification Search
None
See application file for complete search history.

(56) References Cited

U.S. PATENT DOCUMENTS

| 6,111,313 | A  | * | 8/2000  | Kutlu .......................... 257/697 |
| 6,351,031 | B1 | * | 2/2002  | Iijima et al. .................. 257/698 |
| 7,342,317 | B2 | * | 3/2008  | Ho et al. ...................... 257/774 |
| 7,893,527 | B2 | * | 2/2011  | Shin et al. .................... 257/698 |
| 2007/0007983 | A1 | | 1/2007 | Salmon |
| 2008/0029872 | A1 | * | 2/2008 | Hsu et al. ..................... 257/690 |
| 2008/0116565 | A1 | * | 5/2008 | Hsu et al. ..................... 257/699 |
| 2008/0116569 | A1 | | 5/2008 | Huang et al. |
| 2008/0185704 | A1 | * | 8/2008 | Hsu et al. ..................... 257/690 |
| 2008/0308917 | A1 | | 12/2008 | Pressel et al. |
| 2010/0072606 | A1 | * | 3/2010 | Yang ............................ 257/692 |
| 2010/0078655 | A1 | * | 4/2010 | Yang ............................ 257/81 |

OTHER PUBLICATIONS

International Search Report and Written Opinion dated Jun. 19, 2012 for related PCT Patent Application No. PCT/US2012/028300.

* cited by examiner

*Primary Examiner* — Alonzo Chambliss
(74) *Attorney, Agent, or Firm* — Jihan A. R. Jenkins, Esq.; Ryan A. Schneider, Esq.; Troutman Sanders LLC

(57) ABSTRACT

The various embodiments of the present invention provide a novel chip-last embedded structure, wherein an IC is embedded within a one to two metal layer substrate. The various embodiments of the present invention are comparable to other two-dimensional and three-dimensional WLFO packages of the prior art as the embodiments have similar package thicknesses and X-Y form factors, short interconnect lengths, fine-pitch interconnects to chip I/Os, a reduced layer count for re-distribution of chip I/O pads to ball grid arrays (BGA) or land grid arrays (LGA), and improved thermal management options.

26 Claims, 14 Drawing Sheets

CHIP-LAST EMBEDDED INTERCONNECT STRUCTURES

CROSS-REFERENCE TO RELATED APPLICATION

This application claims the benefit of U.S. Provisional Patent Application Ser. No. 61/450,432, filed 8 Mar. 2011, which is incorporated herein by reference in its entirety as if fully set forth below.

BACKGROUND

1. Field

The various embodiments of the present invention relate to chip-last embedded interconnect structures and methods of making the same.

2. Description of Related Art

The trend in miniaturized and highly-functional electronic modules is driving the need for embedded actives and passives that enables highly-complex heterogeneous sub-systems and systems. Two-types of embedding technologies currently exists, both of which are based on "chip-first" techniques and include (1) embedding by wafer-level fan-out (WLFO), and (2) embedding in organic substrates. Alternative technology, called "chip-last" technology has the potential to overcome manufacturing and business challenges of chip-first technology, however chip-last technology also presents challenges. For example, the fabrication of multiple substrate layers and cavity formation for the chip can be difficult, and the associated cost of the substrate can be relatively high, and thus undesirable.

Therefore, there is a need for a chip-last technology that addresses these problems. It is to this need that the present invention is directed. Specifically, the invention disclosed herein addresses the limitations listed above using chip-last embedding technology yet retains the benefits of and achieves a structure similar to the WLFO structure of the prior art.

BRIEF SUMMARY

Various embodiments of the present invention provide an embedded integrated circuit (IC) package structure, comprising a substrate having a first side and a second side; a dielectric layer disposed on the first side of the substrate, wherein the dielectric layer defines a cavity, the cavity being configured to receive and embed an IC; a plurality of through-vias defined within the substrate extending at least from the first side of the substrate to the second side of the substrate, wherein the through-vias also act as bonding pads to electrically interconnect the active IC to the second side of the substrate; and a metal redistribution layer comprising a plurality of fan-out routing wires disposed on the second side of the substrate configured to interconnect the active IC to a circuit board or to other IC packages.

The plurality of through-vias may be less than about 150 µm center to center in pitch and the overall thickness of the embedded IC package structure may be less than about 250 µm.

The active surface of the active IC may be on the bottom of the active IC or on the top of the active IC.

The active IC may be matched in thickness to the cavity defined within the dielectric layer.

The top surface of the IC and the top surface of the cavity may be co-planar such that the IC is embedded within the dielectric layer.

The substrate may be about 30 µm to about 250 µm in thickness. Further, the plurality of through-vias may be bumpless. The structure may further comprise a plurality of bumps connected to I/O pads on the active surface of the active IC. The structure may even further comprise bonding pads disposed on the first side of the substrate and aligned with the cavity for electrically interconnecting the plurality of bumps to the through vias.

The plurality of bumps may be made of copper, solder, tin, other metal alloys, electrically conductive pastes or any combination thereof. The substrate may be made of a polymer-glass composite material, a glass material, a glass-reinforced polymer material, silicon, or combinations thereof. Further, the plurality of through-vias may be filled with copper and/or an additional metal or alloy, wherein the metal or alloy is selected from a group comprising of tin, tin-silver, tin-copper, tin-silver-copper, or any other metal or alloy with a melting point below about 300° C.

In another exemplary embodiment, the embedded integrated circuit (IC) package structure may comprise a substrate having a first side and a second side, the substrate being about 25 to about 250 micrometers in thickness; a dielectric layer having a first side and a second side, wherein the second side of the dielectric layer is disposed on the first side of the substrate, and wherein the dielectric layer defines a cavity to receive and embed a first IC; a first plurality of through-vias defined within the substrate extending at least from the first side of the substrate to the second side of the substrate and aligned with the cavity, wherein the first plurality of through-vias also act as bonding pads to electrically interconnect a plurality of I/O pads disposed on an active surface of the first IC to the second side of the substrate; a first metal redistribution layer comprising a plurality of fan-out routing wires disposed on the second side of the substrate configured to interconnect the first IC to a circuit board or to other IC packages; a second metal redistribution layer comprising a plurality of fan-out routing wires disposed on the first side of the dielectric layer also configured to interconnect the first IC to additional ICs or to other IC packages; and a second plurality of through-vias defined within the substrate and the dielectric layer extending at least from the second side of the substrate to the first side of the dielectric layer to electrically connect a plurality of I/O pads disposed on an active surface of the second IC to the second side of the substrate.

The active surface of the active IC may be on the bottom of the active ICs or on the top of the active ICs.

In some embodiments, the first plurality of through-vias may be less than about 150 µm center to center in pitch and the overall thickness of the embedded IC package may be less than about 250 µm.

The first IC may be matched in thickness to the cavity, such that the first IC and the top surface of the cavity are co-planar.

In some embodiments, the structure may further comprise a second IC assembled on the first side of the dielectric layer and electrically connected to the first IC.

Lastly, the plurality of first and second through-vias may be bumpless.

DETAILED DESCRIPTION

Figure 1:
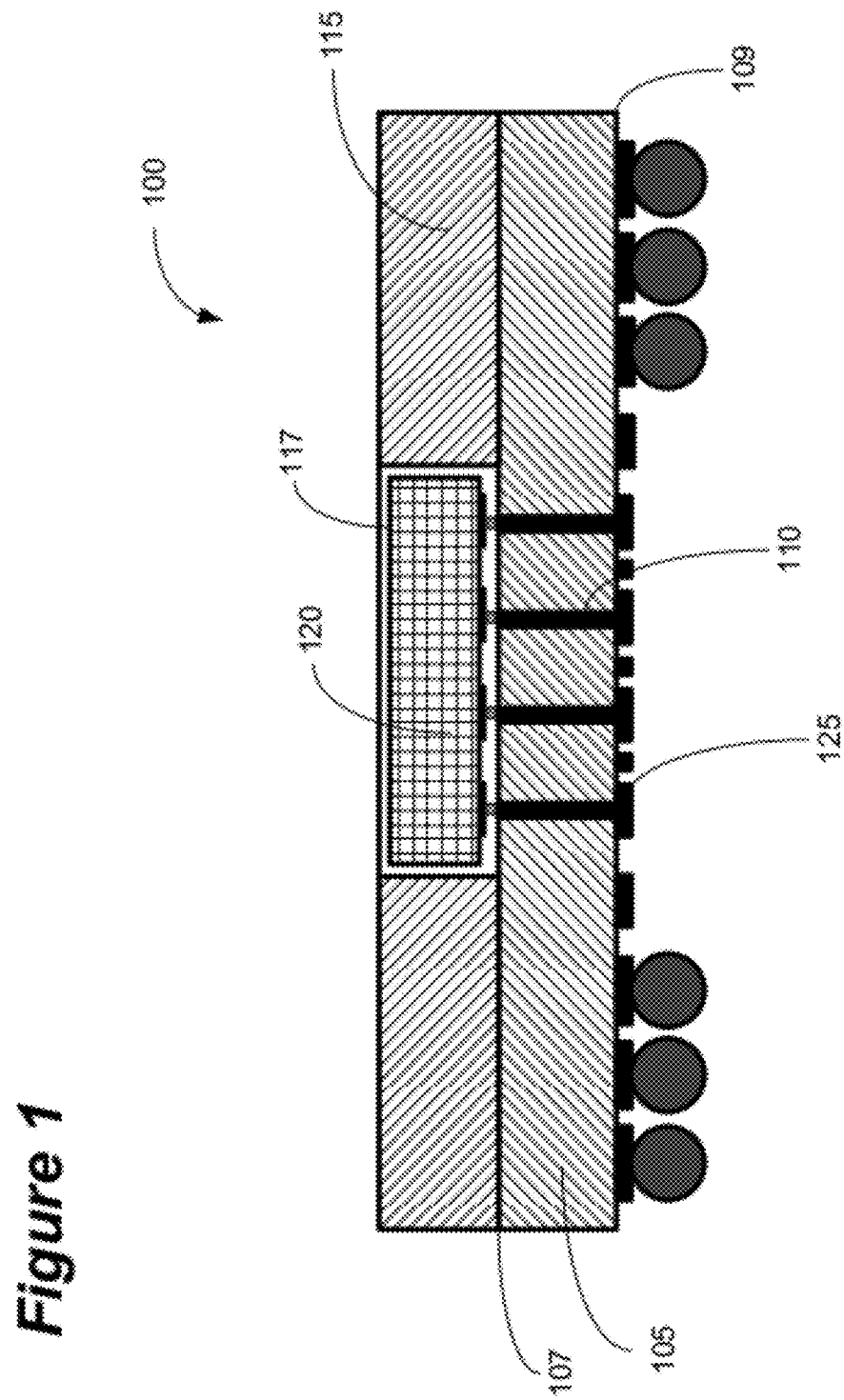
FIG. 1 illustrates an exemplary embodiment of a one-metal layer chip-last package in accordance with the present invention.

Referring now to the figures, wherein like reference numerals represent like parts throughout the several views, exemplary embodiments of the present invention will be described in detail. Throughout this description, various components can be identified as having specific values or parameters, however, these items are provided as exemplary embodiments. Indeed, the exemplary embodiments do not limit the various aspects and concepts of the present invention as many comparable parameters, sizes, ranges, and/or values can be implemented.

It should also be noted that, as used in the specification and the appended claims, the singular forms "a," "an," and "the" include plural references unless the context clearly dictates otherwise. For example, reference to a component is intended also to include composition of a plurality of components. References to a composition containing "a" constituent is intended to include other constituents in addition to the one named. Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Values may be expressed herein as "about" or "approximately" one particular value, this is meant to encompass the one particular value and other values that are relatively close but not exactly equal to the one particular value. By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

It shall also be understood that the terms "package," "structure," and "interconnect structure" may be used interchangeably and refer to devices that can be used for connecting electronic components across one or more of the generally accepted six levels of interconnect in an electronic system. It shall further be understood that the term integrated circuit (IC) chip encompasses chips, sensors, dies, ICs, etc.

The various embodiments of the present invention provide a novel chip-last embedded structure, wherein an IC is embedded within a one to two metal layer substrate. The various embodiments of the present invention are comparable to other two-dimensional and three-dimensional WLFO packages of the prior art as the embodiments have similar package thicknesses and X-Y form factors, short interconnect lengths, fine-pitch interconnects to chip I/Os, a reduced layer count for re-distribution of chip I/O pads to ball grid arrays (BGA) or land grid arrays (LGA), and improved thermal management options.

The embodiments of the present invention, however, offer significant advantages over the prior art as well as it: (1) provides selective site embedding, (2) provides intermediate testability for multi-die packages, (3) has improved thermo-mechanical stress management, (4) is scalable to large panel manufacturing due to a much lower sensitivity to die placement accuracy and panel dimensional instability, (5) has reduced package manufacturing cycle time due to parallel fabrication of substrate and IC interconnects, (6) has reduced costs due to the elimination of over-molding and build-up RDL processes, (7) facilitates ultrathin subsystems, (8) enables double-side wiring for improved interconnect reliability, (9) allows for repairs to be made after assembly, if necessary, (10) allows for heterogeneous integration of embedded dies, thin film passives, IPDs, and discrete passives of different thicknesses and materials, and (11) enables effective heat transfer due to the exposed die.

Referring to FIG. 1, there is shown an exemplary embodiment of a one-metal layer chip-last package 100 in accordance with the present invention. Specifically, there is shown a substrate 105 having a first side 107 and a second side 109. The substrate 105 is an ultra-thin and low-cost organic substrate. For example, the substrate 105 can be about 25 to about 250 micrometers (μm) in thickness. In preferred embodiments, however, the substrate 105 is about 30 μm in thickness. Further, the substrate 105 can be made of many materials. For example, but in no way limiting, the substrate 105 can be made of a polymer-glass composite material, a glass material, a glass reinforced polymer material, silicon, or combinations thereof.

A plurality of through-vias 110 can be defined within the substrate 105 such that they extend at least from the first side 107 of the substrate 105 to the second side 109 of the substrate 105. In exemplary embodiments, the plurality of through-vias 110 have a diameter ranging from about 25 to about 50 μm, and are less than about 150 μm center to center in pitch. The plurality of through-vias 110 can be partially, substantially, or completely filled with a metal, for example but not limited to, copper, and an additional metal and/or alloy. The additional metal and/or alloy can be selected from a group comprising of tin, tin-silver, tin-copper, tin-silver-copper, or any other metal or alloy with a melting point below about 300° C.

As further illustrated, a dielectric layer 115 is disposed on the first side 107 of the substrate 105. The dielectric layer 115 defines a cavity 117, which is aligned with the plurality of through-vias 110, wherein the cavity 117 is configured to receive and embed an active IC-chip 120. It shall be understood that the cavity 117 can be pre-defined before the dielectric layer 115 is disposed on the first side 107 of the substrate 105, which reduces cavity formation cost. Or, alternatively, the cavity 117 can be defined after the dielectric layer 115 is disposed on the first side 107 of the substrate 105, which is further described below. The dielectric layer 110 can be made of the same materials as the substrate 105, described above, or can be made of different materials, for example reinforced polymers, non-reinforced polymers, inorganic dielectric materials, or combinations thereof.

An IC-chip 120 can then be disposed within the cavity 117. The size and configuration of the IC-chip is one that substantially mirrors the size and width of the cavity 117, such that the top surface of the IC-chip 120 is coplanar with the top surface of the dielectric layer 110, thus effectively embedding the IC-chip 120. The IC-chip comprises an active surface, which is adjacent the first side 107 of the substrate 105, which can further comprise a plurality of I/O pads. It shall be understood that the IC-chip 120 is substantially, if not completely, embedded within the dielectric layer 110. This embedded configuration reduces the overall size of the package assembly as it eliminates the need for additional build-up layers and mold compounds, as in the prior art. In exemplary embodiments, the total package thickness is less than about 250 μm, and more specifically less than about 150 μm which facilitates ultra-fine pitch, for example, about 70 μm pitch.

Figure 2:
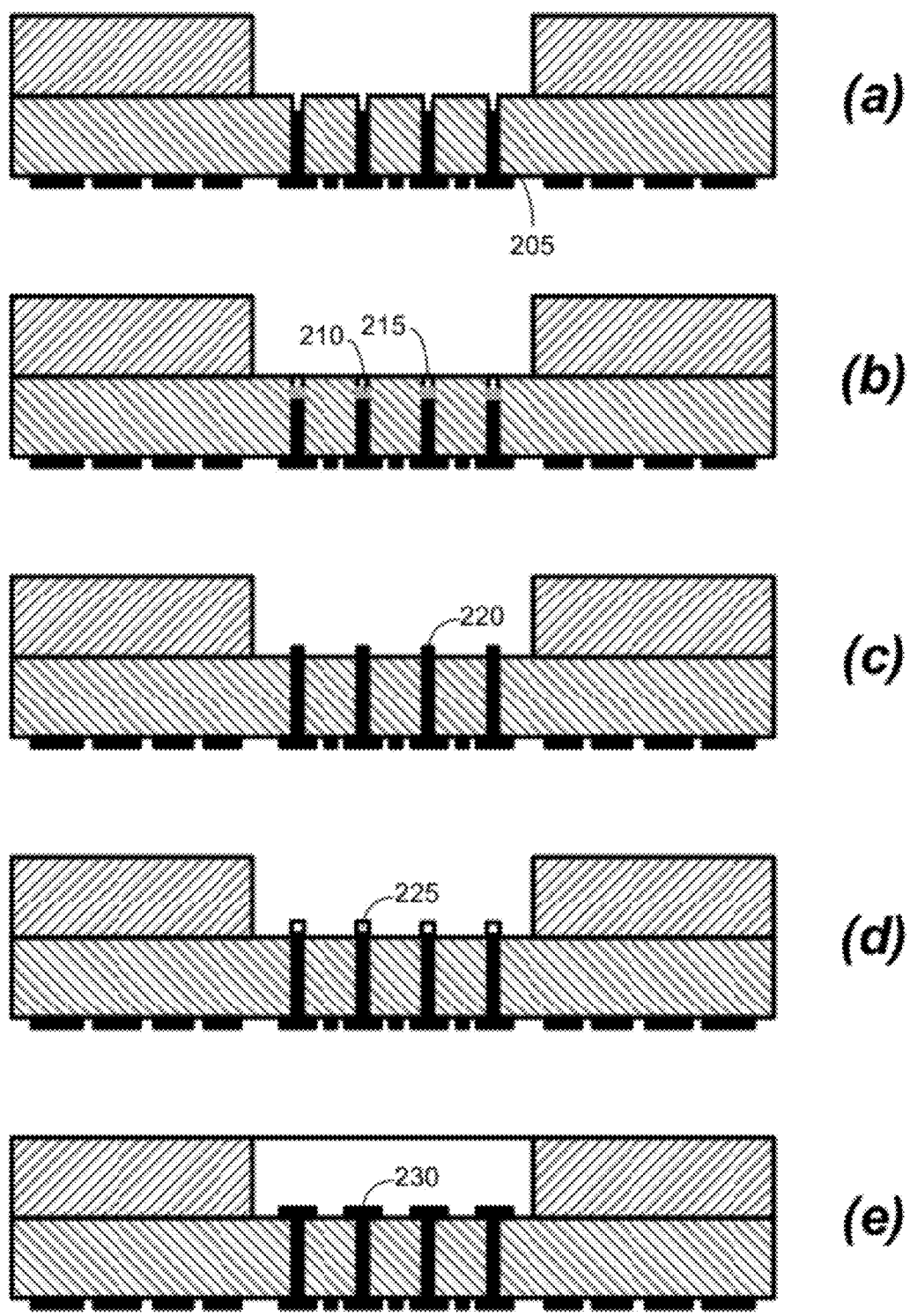
FIGS. 2a-e illustrate exemplary embodiments of the one-metal layer chip-last package comprising various interconnect structures in accordance with the present invention.

Referring now to FIG. 2a, there is shown substantially-filled through-vias 205. It shall be understood that while the plurality of through-vias can be bumpless and directly bonded to bonding pads disposed on the first side 107 of the substrate 105 to electrically interconnect the active IC-chip surface (via I/O pads disposed thereon) to the second side of the substrate, the plurality of through-vias can also further comprise additional interconnect components, as illustrated in FIGS. 2b-e. In some embodiments, and as illustrated in FIG. 2b, buried metal studs 210 along with solder caps 215 as interconnects can be placed inside the through-vias above the metal filling, such that they are adjacent and aligned with the active surface of the IC-chip but do not extend beyond the surface level of the first side 237 of the substrate 235. In alternative embodiments, and as illustrated in FIG. 2c, buried metal studs with bumps 220 as interconnects may be placed on and above the surface level of the first side 237 of the substrate 235. In yet other embodiments, and as illustrated in FIG. 2d, buried metal studs with solder caps 225 as interconnects may be placed higher than the surface level of the first side 237 of the substrate 235. In other embodiments, and as illustrated in FIG. 2e, buried metal studs with pads 230 as interconnects may be placed on and above the surface level of the first side 237 of the substrate 235. In all embodiments of the present invention, the buried metal studs and the solder caps/pads provide fine-pitch interconnectivity to the IC-chip. Further, it shall be understood that, unlike in certain prior art embodiments, solder bumps and pads are not required to facilitate electrical connectivity to the IC-chip, which consequently reduces manufacturing costs and size. In fact, in some embodiments, the through-vias can interconnect the IC-chip without the need for any additional interconnect components, a solder bump or a pad. Further, in embodiments where additional interconnect components, solder bumps, or pads are used, an underfill may be disposed between the IC-chip and the additional interconnect components, solder bumps, or pads.

Figure 3:
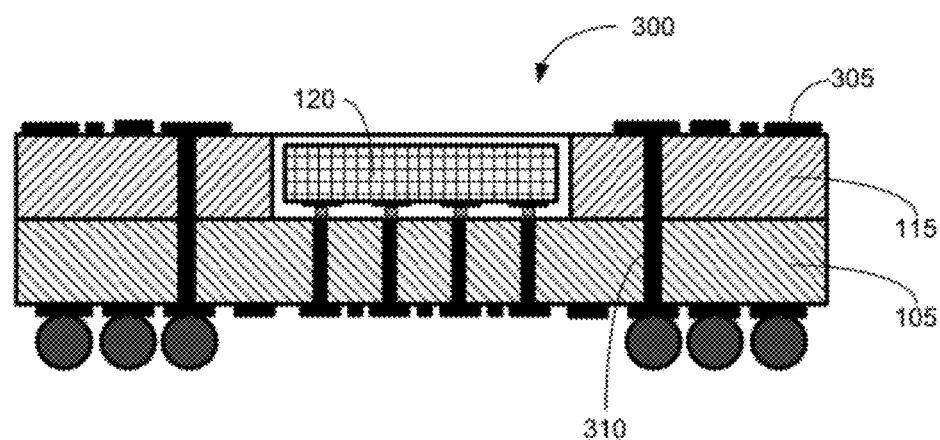
FIG. 3 illustrates an exemplary embodiment of a two-metal layer chip-last package in accordance with the present invention.

Referring back to FIG. 1, a first metal redistribution layer 125 can be disposed on the second side 109 of the substrate 105. The first metal redistribution layer 125 comprises a plurality of ultra-fine and ultra-high density routing wires for fine-chip fanning-out. As illustrated in FIG. 1, there is shown a one-metal layer fan-out package 100, appropriately named as the embodiment has one metal redistribution layer 125. In some embodiments, and as illustrated in FIG. 3, a second metal redistribution layer 305 can be disposed on the top surface of the dielectric layer 115, thereby forming a two-metal layer fan-out package 300. Like the first metal redistribution layer 125, the second metal redistribution layer 305 also comprises a plurality of ultra-fine and ultra-high density routing wires for fine-chip fanning-out. In two-metal layer fan-out packages, a plurality of through vias 310 may also be defined through the substrate 105 and the dielectric layer 115 such that they interconnect the first metal redistribution layer 125 and the second metal redistribution layer 305.

Figure 4:
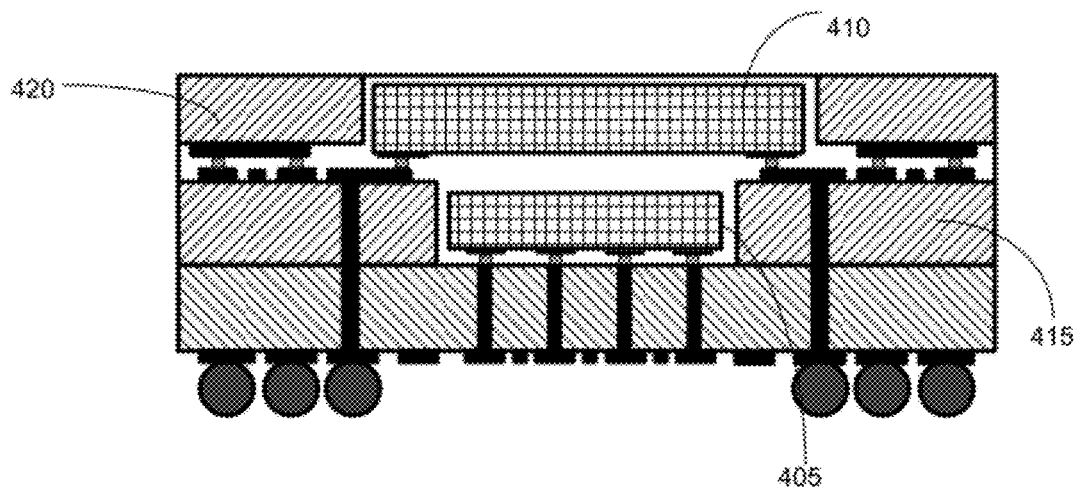
FIG. 4 illustrates an exemplary embodiment of a two-metal layer chip-last package having dual chips in accordance with the present invention.
Figure 5:
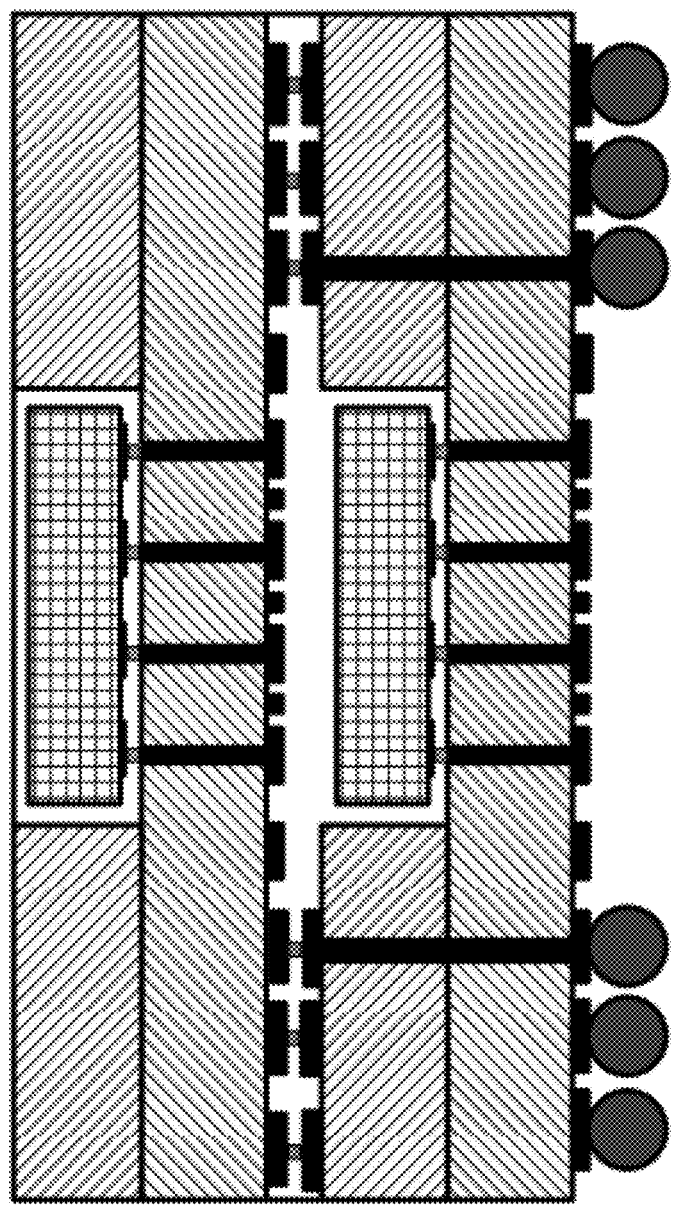
FIG. 5 illustrates an exemplary embodiment of a stacked package in accordance with the present invention.
Figure 6:
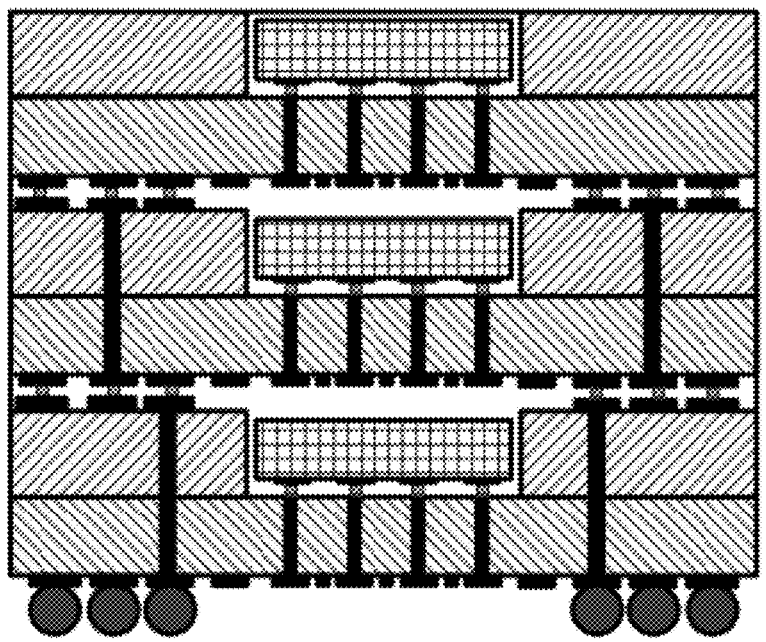
FIG. 6 illustrates an exemplary embodiment of another stacked package in accordance with the present invention.
Figure 7:
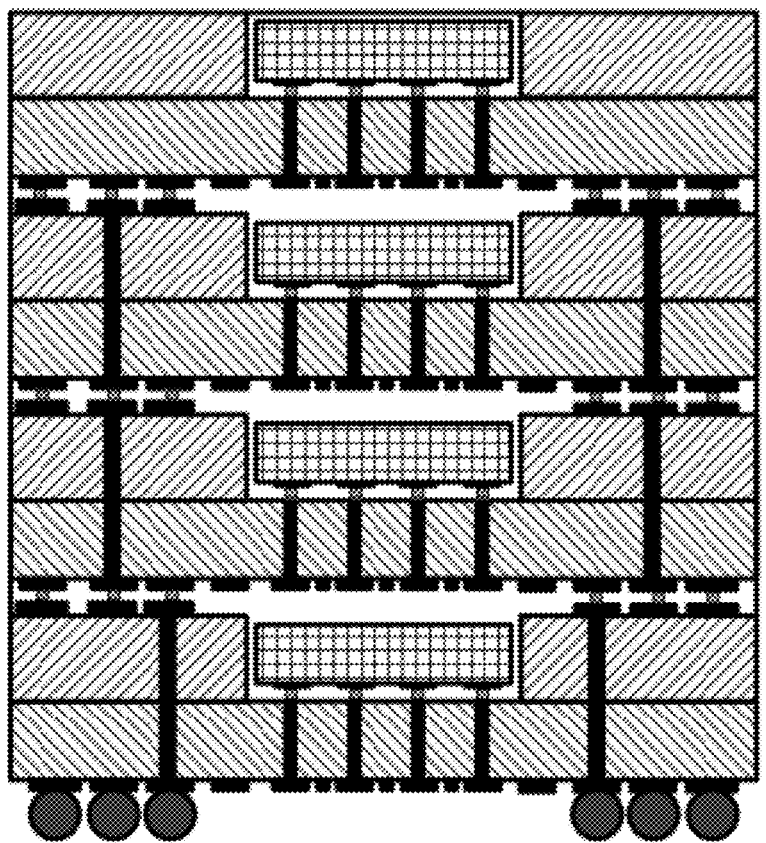
FIG. 7 illustrates an exemplary embodiment of yet another stacked package in accordance with the present invention.

Two-metal layer fan-out packages enable dual-chip embedding in a single package, as illustrated in FIG. 4. In this embodiment, there is shown a first embedded chip 405 and a second embedded chip 410, which are embedded in first 415 and second 420 dielectric layers, respectively. The two-metal layer fan-out substrate 300 can be used for three-dimensional chip stacking, package-on-package stacking, and side-by-side package stacking. FIGS. 5-7 illustrate exemplary embodiments of package-on-package stacking. As further illustrated in FIGS. 5-7, an adhesive 505 may be disposed between packages to enhance connectivity.

Figure 8:
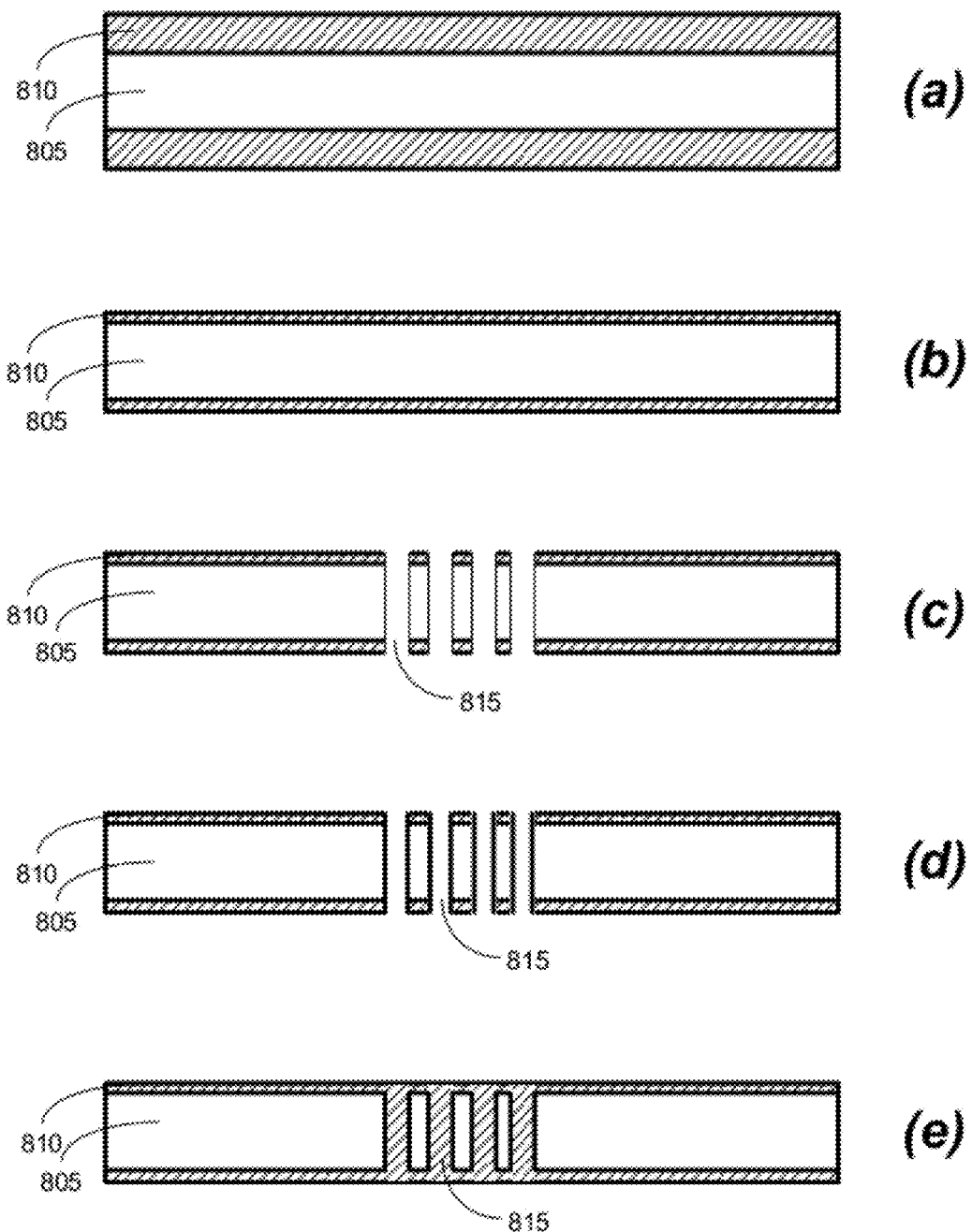
FIGS. 8a-e illustrate exemplary methods of making fine-pitch through vias in accordance with the present invention.

Referring to FIGS. 8a-e, there is shown an exemplary method of making fine-pitch through vias. As illustrated in FIG. 8a, an organic substrate 805 is first provided having a metal foil 810 disposed on both the top side and the bottom side. The metal can be, for example but not limited to, clad copper foil. As illustrated in FIG. 8b, the metal foil 810 can be subsequently thinned down, such that the metal foil is about three to six micrometers on each side of the organic substrate 805. As illustrated in FIG. 8c, the plurality of through vias 815 can then be defined using, for example but not limited to, ultra-violet laser ablation techniques. The through vias 815 are then desmeared and filled using, for example but not limited to, electroless copper plating techniques, as illustrated in FIGS. 8d and 8e, respectively.

Figure 9:
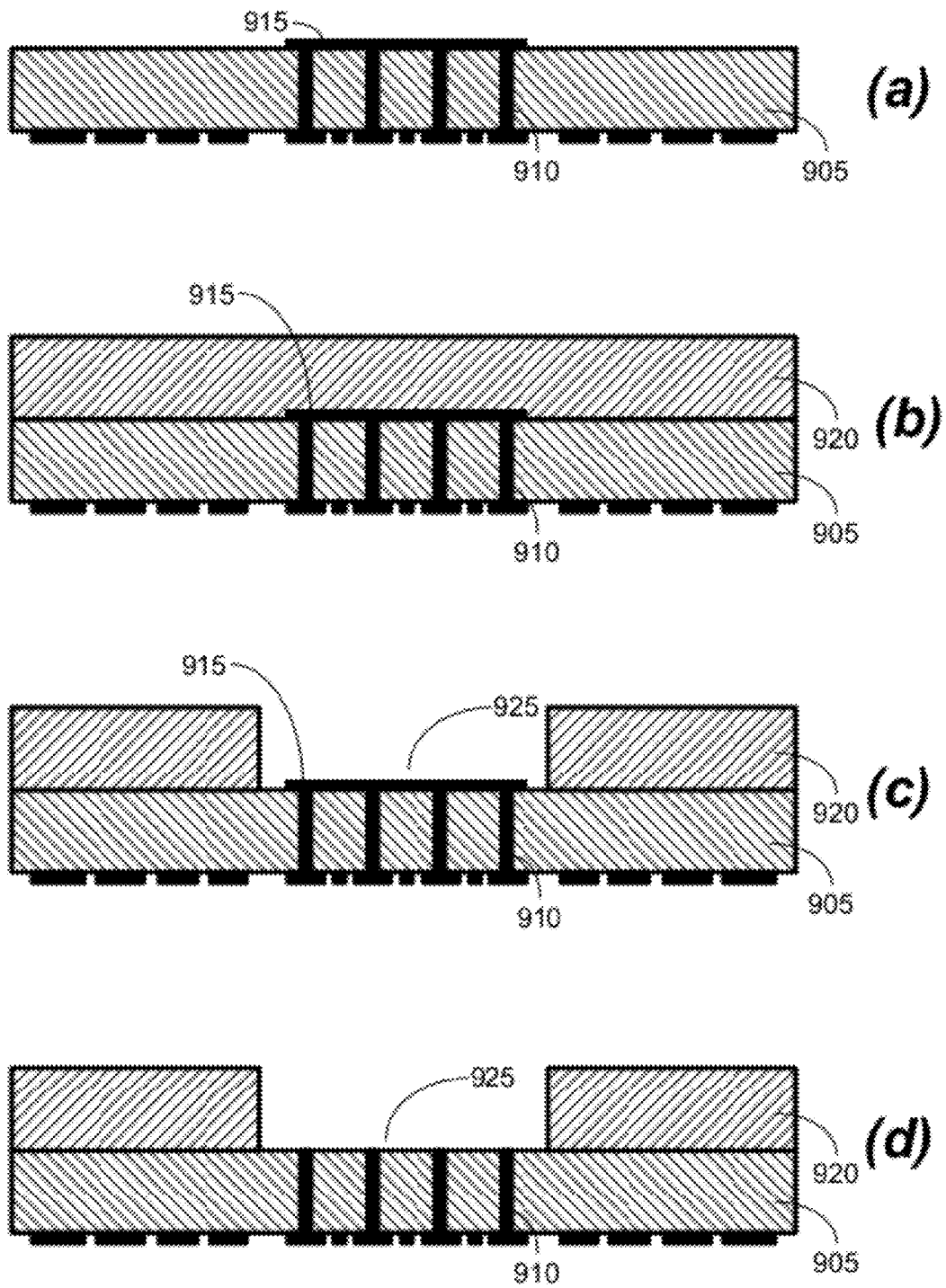
FIGS. 9a-d illustrate exemplary methods of forming a post-cavity with a thin metal protection layer in accordance with the present invention.

After the fine-pitch through vias are formed and the dielectric layer is disposed on the substrate, the cavity within the dielectric can be formed. Referring to FIGS. 9a-9d and FIGS. 10a-10c, there is shown an exemplary method of post-cavity formation with and without thin metal protection, respectively. As illustrated in FIG. 9a, there is shown an organic substrate 905 defining a plurality of through-vias 910 and having a thin metal protection layer 915 on the top surface and aligned with the plurality of through-vias. As illustrated in FIG. 9b, a dielectric layer 920 can be disposed on the top surface of the substrate 905, wherein the metal protection layer 915 is between both the dielectric layer 920 and the substrate 905. As illustrated in FIG. 9c, a cavity 925 can be subsequently defined within the dielectric layer 920 such that the cavity is aligned with the metal protection layer 915 and the plurality of through-vias 910. Lastly, referring to FIG. 9d, the metal protection layer 915 can be subsequently removed.

Figure 10:
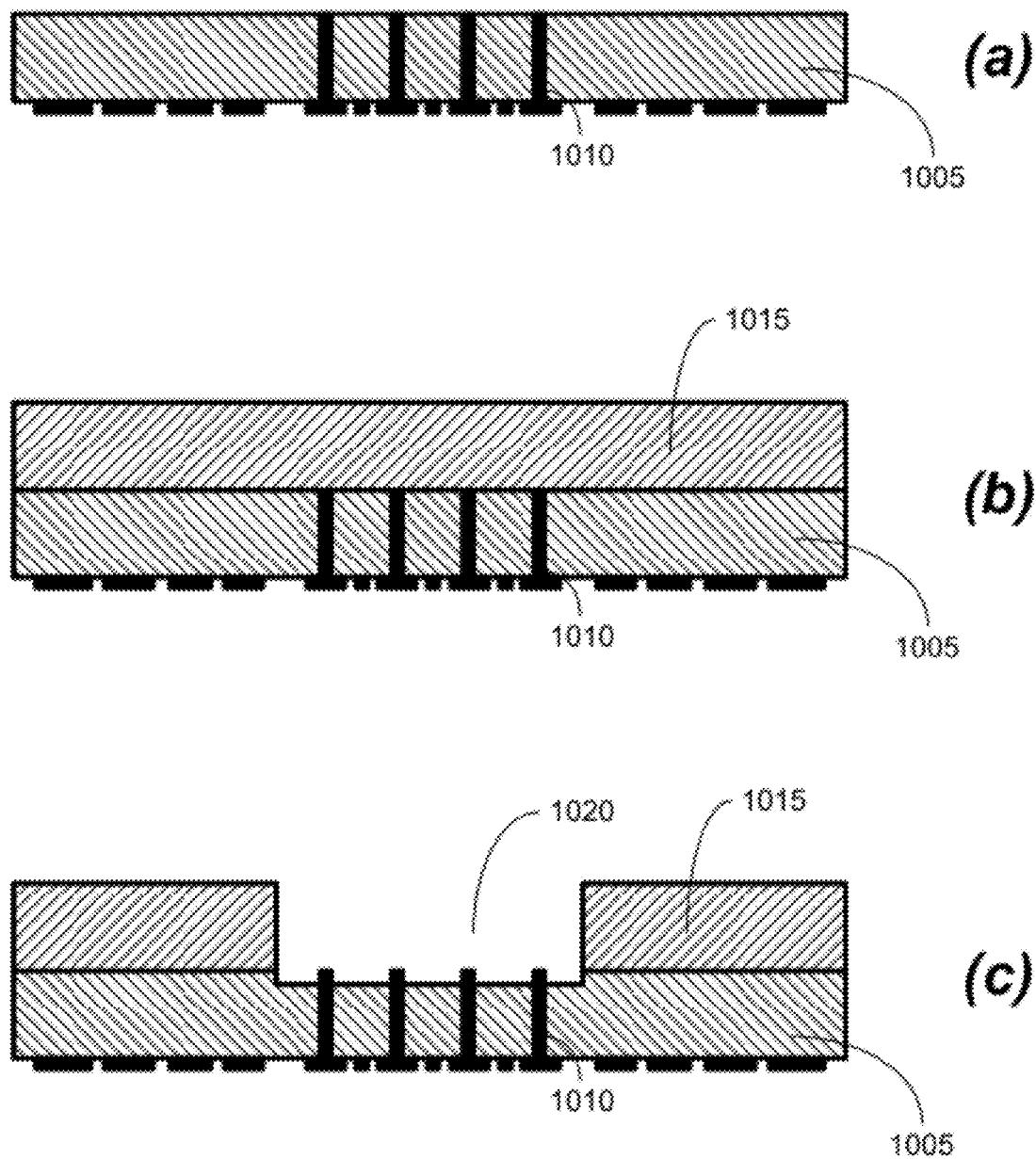
FIGS. 10a-c illustrate exemplary methods of forming a post-cavity without a thin metal protection layer in accordance with the present invention.

As illustrated in FIG. 10a, there is shown an organic substrate 1005 defining a plurality of through-vias 1010. It shall be understood that unlike the illustration in FIG. 9a, the illustration in FIG. 10a does not include a thin metal protection layer. As illustrated in FIG. 10b, a dielectric layer 1015 can be disposed on the top surface of the substrate 1005 and a cavity 1020 can be defined within the dielectric layer 1015, as illustrated in FIG. 10c.

Figure 11:
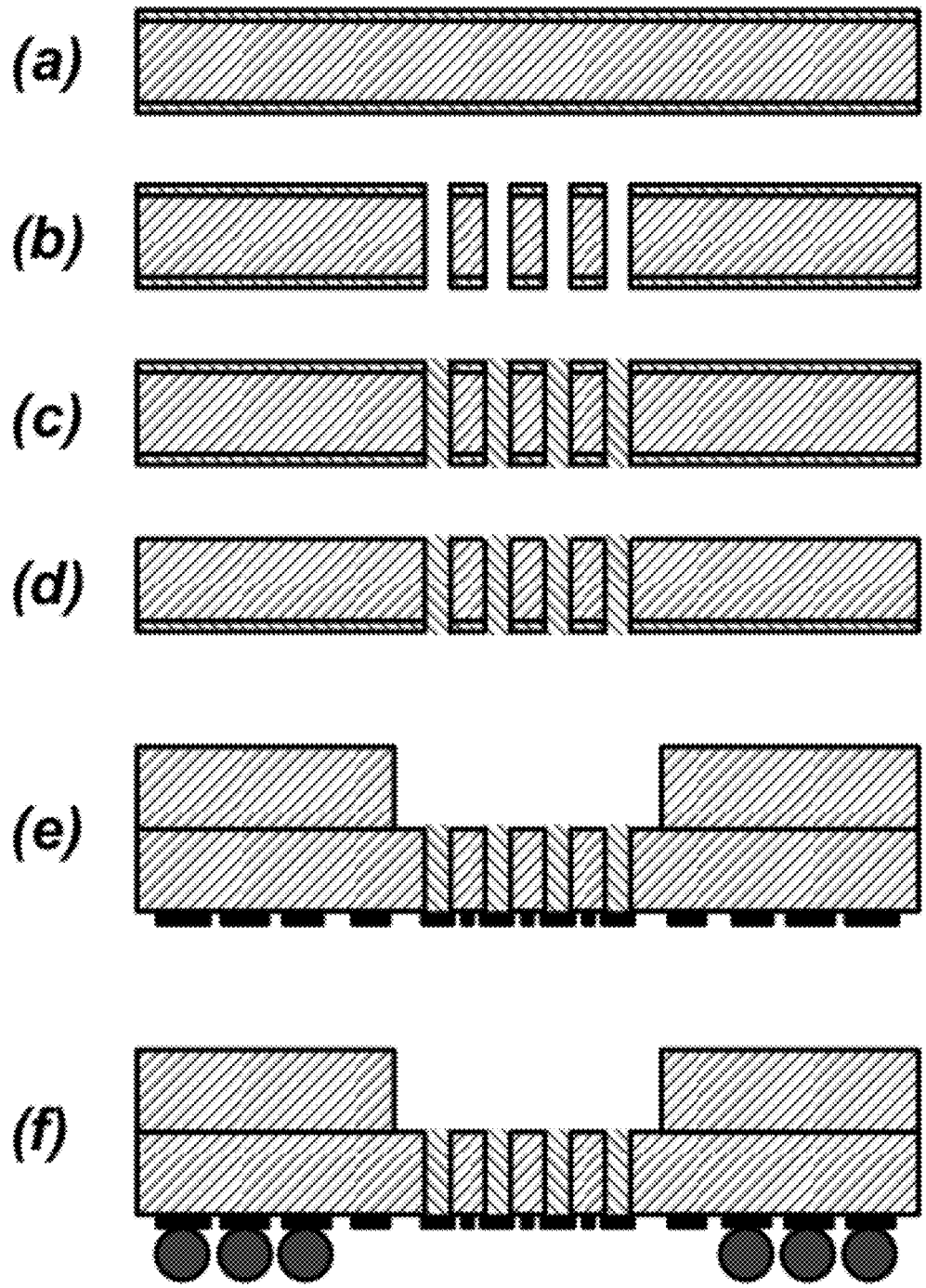
FIGS. 11a-f illustrate exemplary methods of making a one-metal layer chip-last package in accordance with the present invention.

Referring to FIGS. 11a-f and 12a-f, there is shown exemplary methods of fabricating one-metal layer and two-metal layer package embodiments, respectively. First, a thin core substrate is provided, as illustrated in FIG. 11a. The plurality of through-vias are defined within the substrate, as illustrated in FIG. 11b. The plurality of through-vias are filled with a metal, for example copper, as illustrated in FIG. 11c. Next, the top side of the substrate is etched, as illustrated in FIG. 11d, and a dielectric layer is disposed thereon, illustrated in FIG. 11e. It shall be understood that in this exemplary method, the cavity has been pre-defined within the dielectric layer. Fine lines can then be formatted by fine-line subtractive or by semi-additive processes on the bottom surface of the substrate, also illustrated in FIG. 11e. Finally, solder balls can be attached, as illustrated in FIG. 11f.

Figure 12:
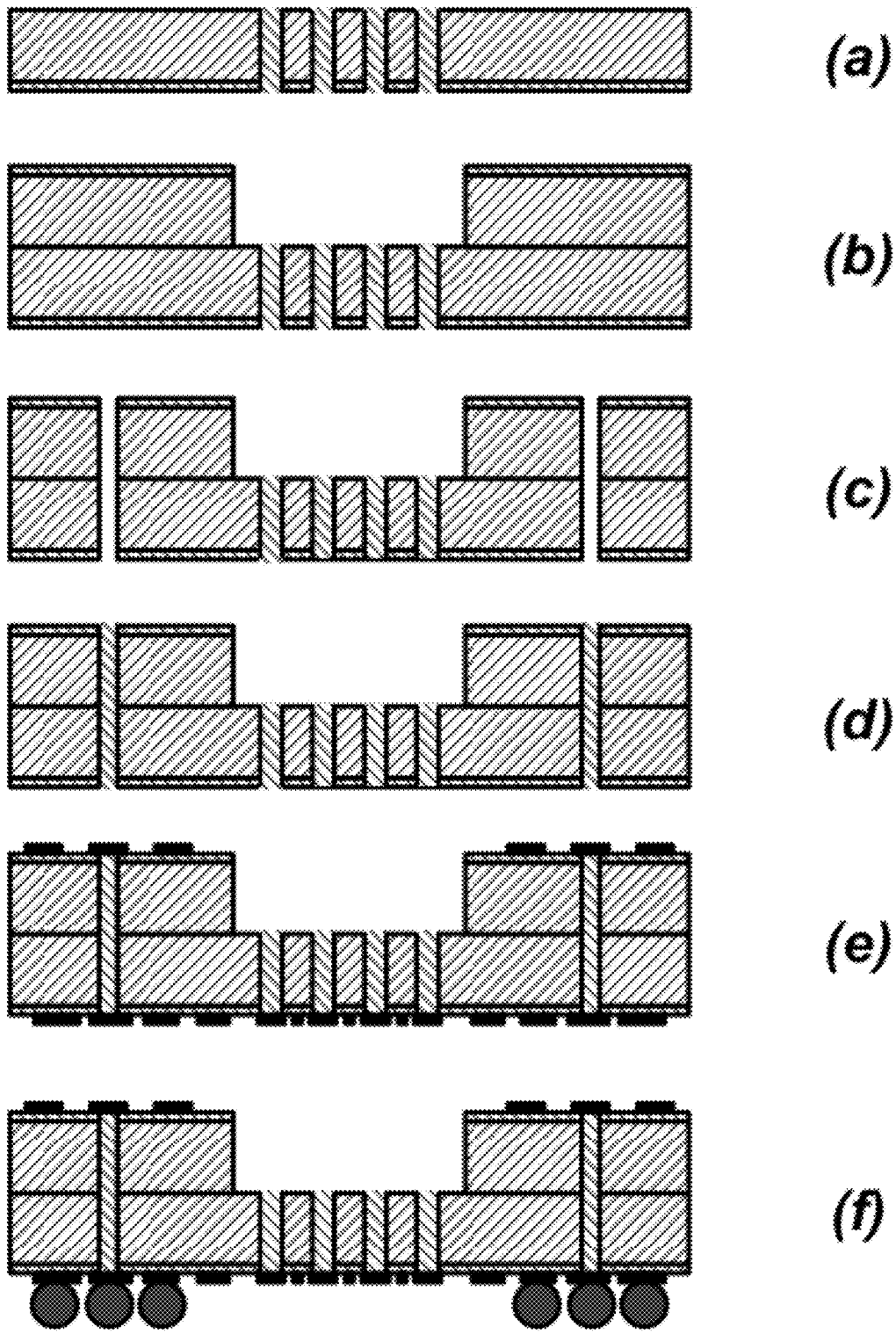
FIGS. 12a-f illustrate exemplary methods of making a two-metal layer chip-last package in accordance with the present invention.

Referring to FIG. 12a, there is shown a substrate defining a plurality of through-vias, wherein the top surface has been etched. A dielectric defining a pre-cut cavity and having a metal layer disposed on the top surface is then disposed on the top surface of the substrate, as illustrated in FIG. 12b. Subsequently, a plurality of through-vias are defined extending from the first metal layer to the second metal layer, illustrated in FIG. 12c. The plurality of through-vias are then plated, illustrated in FIG. 12d, and fine lines are formed within the first and second metal layers by fine line subtractive or semi-additive processes, as illustrated in FIG. 12e. Finally, solder balls can be attached, as illustrated in FIG. 12f.

Figure 18:
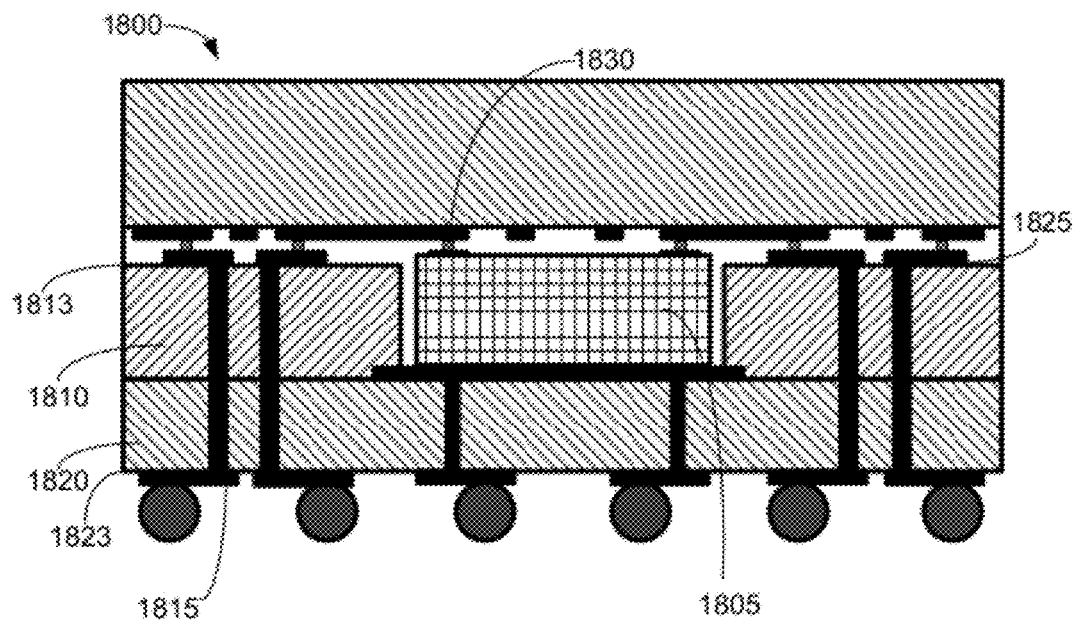
FIG. 18 illustrates an alternative embodiment of the present invention, wherein the active surface of the IC-chip is disposed on the top of the IC-chip.
Figure 19:
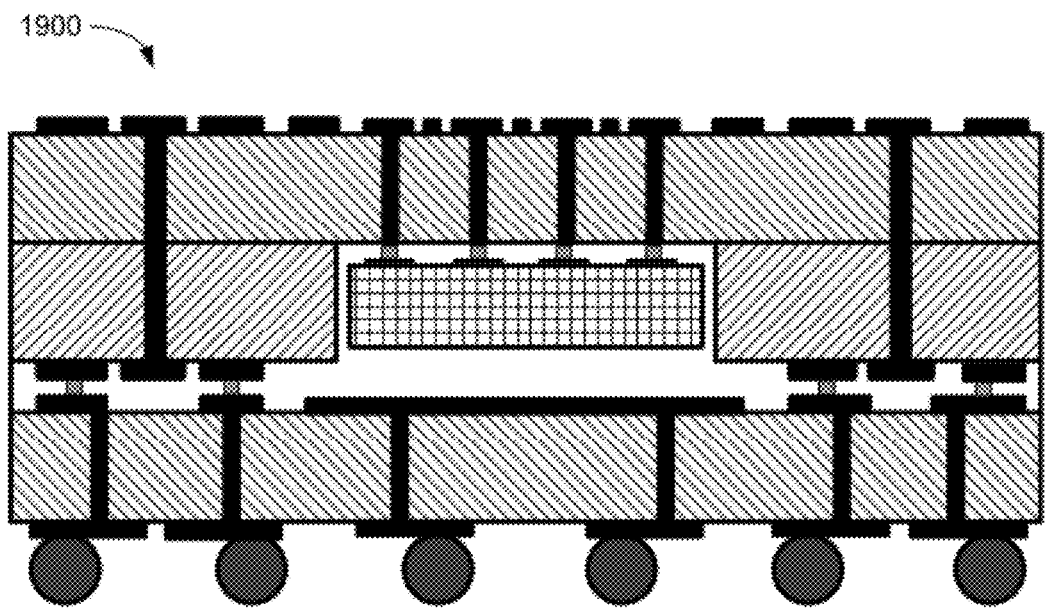
FIG. 19 illustrates yet another alternative embodiment of the present invention, wherein the active surface of the IC-chip is disposed on the top of the IC-chip.

Referring to FIG. 18, there is shown an alternative embodiment of the present invention 1800. In the embodiments described above, the IC-chip's active surface was adjacent the first side of the substrate, and therefore on the "bottom" of the chip. In alternative embodiments, however, the IC-chip 1805 comprises an active surface on the "top" of the chip. As illustrated in FIG. 18, the IC-chip 1805 remains embedded within a pre-defined cavity in the dielectric layer 1810. Further, the embodiment comprises a first metal redistribution layer 1815 disposed on a bottom surface 1823 of the substrate 1820 and a second redistribution layer 1825 disposed on a top surface 1813 of the dielectric layer 1810. Each redistribution layer comprises a plurality of ultra-fine and ultra-high density routing wires for fine-chip fanning-out. A plurality of through-vias may be defined through the substrate 1820 and the dielectric layer 1810 to interconnect the redistribution layers. Because the active surface is disposed on the top of the IC-chip 1805, I/O pads 1830, also disposed on the top of the IC-chip, interconnect the IC-chip 1805 to additional electrical components. Referring to FIG. 19, there is shown yet another embodiment 1900 of the present invention, wherein the IC-chip comprises an active surface on the top of the chip.

EXAMPLES

The various embodiments of the present invention are illustrated by the following non-limiting examples.

Example 1

Chip-Last Embedding in 1-2 Metal Layer Structure

To achieve embedding of a 70-100 μm pitch area array I/O IC in core, an innovative two-metal layer substrate with ultra-high wiring density has been developed. The substrate structure is obtained by a two-step process—(1) fabrication of the thin core substrate with fine-pitch through-holes and fine line width and spaces, and (2) lamination of another thin-core substrate with pre-formed cavity for die embedding. This innovative approach has two major novelties—(1) ultra-fine metal lines and spaces on core laminate and (2) ultra-fine pitch through-holes. Instead of conventional wet etching process, the semi-additive process (SAP), usually used for build-up layer to achieve 10 μm and sub-10 μm lines and spaces was employed for fabrication of ultra-fine copper traces on the core. UV laser with 266 nanometers (nm) wavelength was employed for ultra-fine pitch (70-100 μm) through-holes to meet the fine-pitch flip-chip I/O needs.

TABLE 1

Properties of materials used for this study

| Property | BT (Mitubishi Gas Chemical) | RXP-1 (Rogers Corp.) | X-R-1 (Zeon Chemical) |
|---|---|---|---|
| CTE, ppm/° C. | 10-11 | 13-14 | <40 |
| Tg (DMA), ° C. | 230-240 | >300 | |
| Dk (1~110 GHz) | 4.4 | 3.4 | 6.7 |
| Df (1~110 GHz) | 0.006 | 0.004 | 0.003 |
| Water Absorption, % | 0.3 | <0.1 | <0.1 |
| Flame Resistance (Flame Retardant) | V-0 Halogen free | V-0 Halogen Free | V-0 Halogen free |
| Solder Float | >30 (280° C.) | Pass (288° C./10 sec) | |
| Laser Processable | Yes | Yes | Yes |

Various thin laminate cores with glass fiber reinforced materials, the properties of which are listed in Table 1 were used including low CTE BT laminate, a novel low Dk low Df RXP-1 laminate and a novel high Dk low Df X-R-1 laminate. Specifically, BTTM CCL-HL832NSTM, a low CTE laminate from Mitsubishi Gas Chemical® (MGC), was used. Its CTE is 10-11 ppm/° C. The thicknesses used in this study were 50 μm and 100 μm. RXP-1BTM, a low Dk and low Df laminate provided by Rogers Corp®, was also used. Its Dk is <3.0 and its Df is 0.004. The Dk and Df are stable within the range of 1-110 GHz. X-R-1TM, a high Dk and low Df laminate developed at Zeon Corp®, was also used. Its Dk is 6.8, which is similar to that of ceramic substrate and its Df is 0.003. The design rules and targets for the fabrication of the one to two metal layer substrate are listed in Table 2.

TABLE 2

Design rule targets for this study

| Thickness (μm) | Line/Space (μm) | Through Hole Diameter (μm) | Through Hole Pitch (μm) |
|---|---|---|---|
| 50/75/100 | 10-15 | 30-35 | 70-100 |

Example 2

Fine Lines/Spaces on Core

Figure 13:
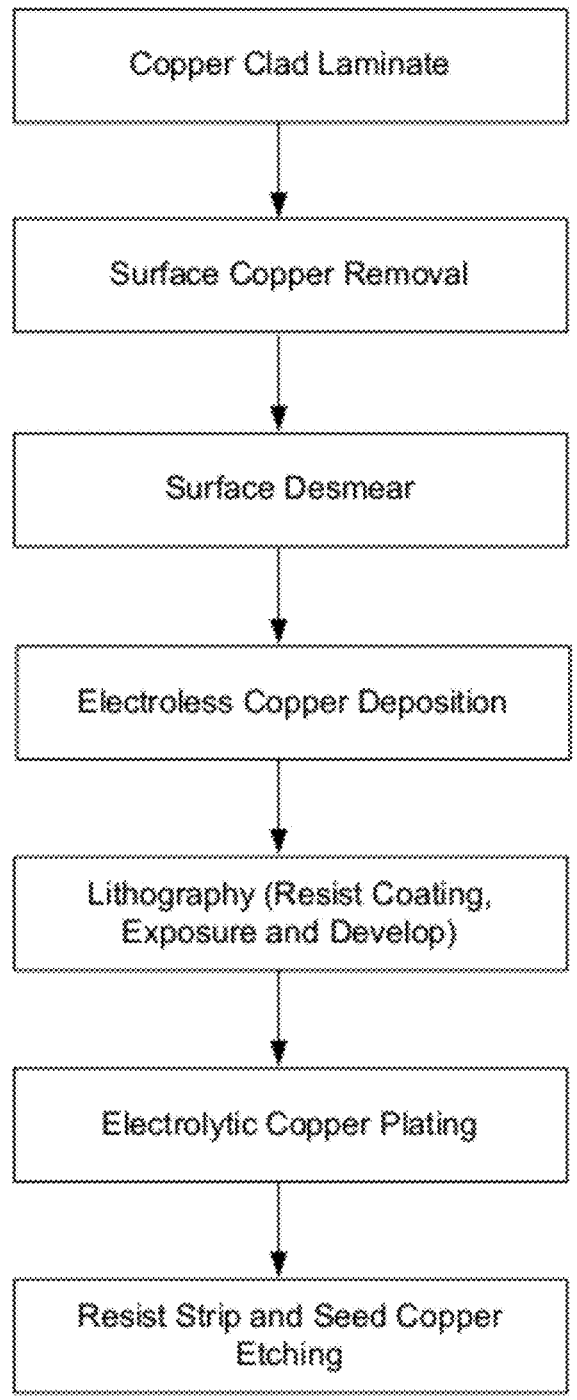
FIG. 13 illustrates an exemplary method of making a thin core substrate in accordance with the present invention.

To fabricate 7-15 μm line widths and spaces for copper circuitry on core laminate, the SAP method was employed instead of the conventional wet etching method. The first step is surface copper removal from a double sided copper clad laminate. Following copper removal, surface desmear and electroless copper plating was done to form a thin copper seed layer on the surface. Thereafter, a layer of dry film photo resist was laminated, exposed, and developed. Once the circuitry pattern was transferred to the photo resist, the electrolytic copper plating was carried out to plate the pattern in the photo-resist mold. After photo resist stripping, the final step is to remove the seed copper layer by micro etching. The process flow is described in FIG. 13.

The process mentioned above enables the wiring density of the 1+2+1 substrate within a two metal layer thin core with filled through holes and ultra fine lines. The reduction in layer count by elimination of build-up layers significantly reduces the substrate cost, thus enabling the organic substrate to be competitive with re-distribution layers used in wafer-level packaging. This research includes use of a state-of-the art electroless and electrolytic copper plating processes to achieve the required ultra-fine line circuitry and through-hole filling. The parameters for these processes have been optimized for next generation dielectrics.

Example 3

Ultra-Fine Pitch Area-Array Through-Holes

The biggest challenge in achieving a substrate structure is fabrication of small diameter through-holes at ultra-fine pitch to meet the chip I/O footprint such that no escape routing is needed on the chip attach side of the module. The concern with ultra-fine pitch area array through-hole fabrication is the wall-to-wall distance of adjacent holes. If the wall-to-wall distance is not large enough, there is a high probability of encountering mechanical strength related issues. Therefore, in order to make ultra-fine pitch area-array through-holes, it is important to fabricate the holes with small diameter.

Currently, two techniques are most commonly used to make through-holes on glass-fiber reinforced laminates—(1) mechanical drilling, and (2) laser drilling. The most established through-hole technology is mechanical drilling. Mechanical drilling is an effective method for through-hole diameters larger than 150 μm. Current the-state-of-the-art mechanical drilling technology can achieve a minimum diameter of 75 μm. Below 150 μm, however, operational cost for mechanical drilling rises exponentially.

Laser drilling removes material by utilizing high power laser beam. The beam can be focused on a small area to vaporize organic and/or inorganic materials through thermal or chemical mechanisms. High power $CO_2$ laser vaporizes the materials by thermal effect due to its long wavelength, for example, 9.4 μm or 10.6 μm infrared radiations. Yttrium-aluminium-garnet (YAG) lasers have short radiations in the ultraviolet range. The typical wavelengths used for drilling are 355 nm and 266 nm. YAG lasers remove material through the break-up of the molecular bonds of the materials because of high energy photons. The energy of a photon $\in$ is equal to hv, where h is Planck's constant and v is the photon's frequency. Since the wavelength is inversely proportional to the frequency, shorter wavelength has higher frequency, therefore higher energy. Due to higher energy, after absorption of the UV light, as in case of YAG lasers, the molecular bonds of the materials break. In addition, UV lasers produce smaller focal spot compared to $CO_2$ lasers which produce larger focal spot. The focal spot becomes critical for ablating smaller areas and achieving smaller diameter through holes.

Figure 14:
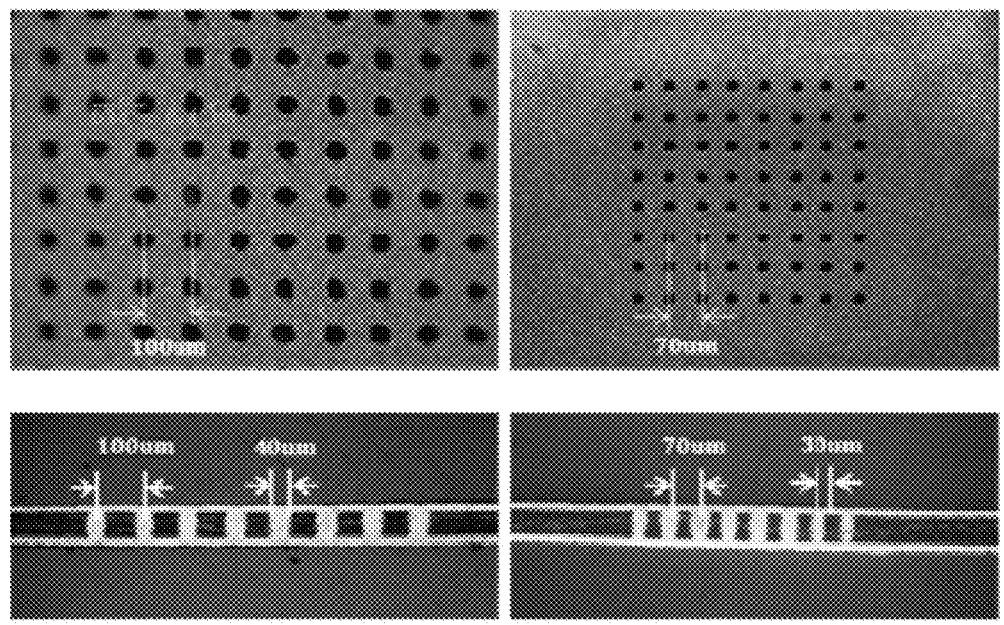
FIG. 14 illustrates cross-sectional images of through-vias in accordance with the present invention.

In this study, YAG UV laser was used for achieving fine sized diameter through-holes. FIG. 14 shows the optical micrographs of 100 μm pitch area-array through-holes and 70 μm pitch area-array though-holes obtained via laser drilling. After laser drilling, the through-holes were filled with copper using a combination of electroless and electrolytic copper plating, the cross-section images of which are also shown in FIG. 14. The images in FIG. 14 show 40 μm through-hole diameter at 100 μm area-array pitch and 30 μm through-hole diameter at 70 μm area-array pitch. In addition, it is clear from FIG. 14 that the optimized process parameters used for copper-filling yielded void-free, fully-filled through-holes even at smaller dimensions and pitches.

Example 4

Substrate Through-Hole Reliability Assessment

Figure 15:
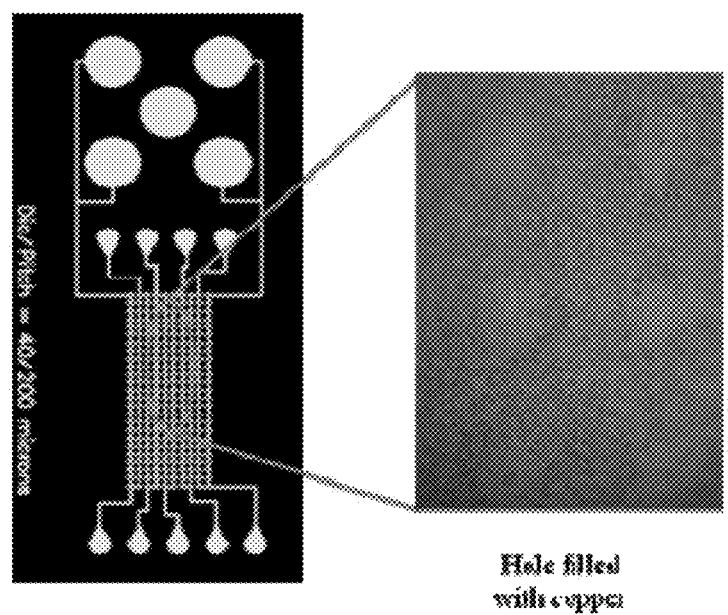
FIG. 15 illustrates daisy chain structures of a package in accordance with the present invention.
Figure 16:
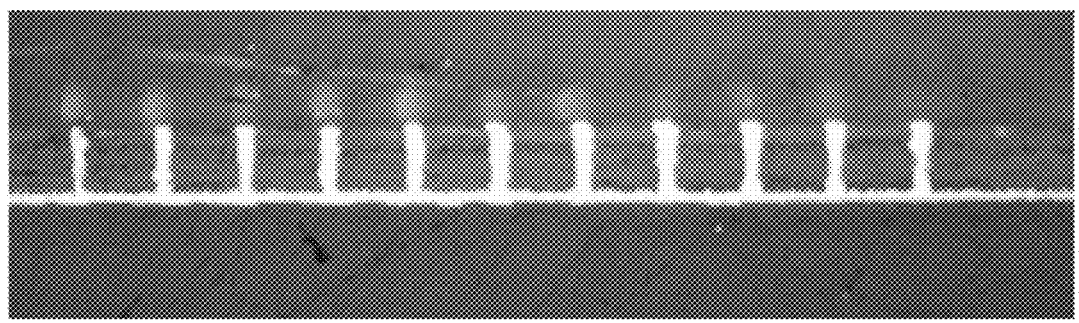
FIG. 16 illustrates a cross sectional image of a row of copper-filled 100 μm very fine pitch through-vias with flat top surfaces as interconnects.
Figure 17:
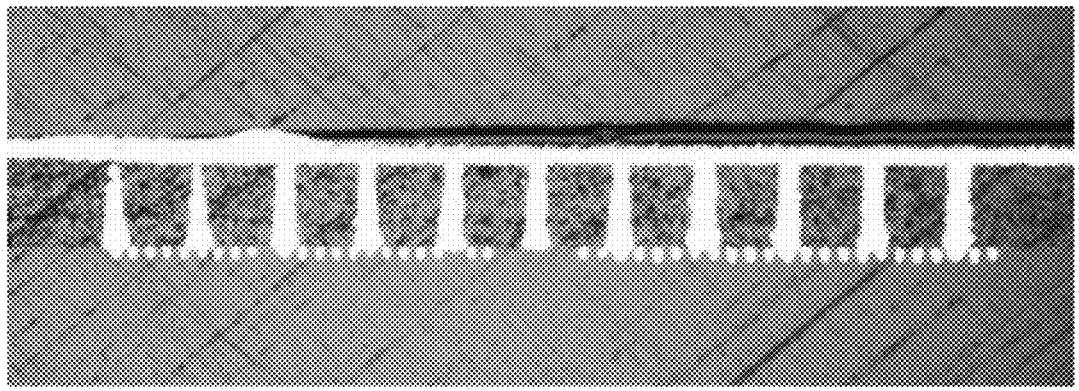
FIG. 17 illustrates a cross sectional image of a row of copper-filled 100 μm very fine pitch through-vias with ultra-fine routing lines and spacings.

Two test boards made of X-R-1TM laminates were designed and fabricated for thermo-mechanical reliability test. The daisy chain structures, shown in FIG. 15 were designed for process evaluations as well as thermal cycling performance assessments. The design includes 50 chains on each board with each chain containing 250 through-holes. The through-hole pitch for reliability assessment was 200 μm as the main rationale behind testing was to test the reliability of smaller diameter vias decoupled with the effects of smaller pitch. Accordingly, the diameters of the through-holes included in the chains were 30, 40, 50, and 60 μm. As mentioned in the previous section, all the through-holes were filled with copper. Design and fabrication of 100 μm pitch area-array through-holes test vehicles is currently ongoing to assess the combined effect of small diameter and pitch of through-holes.

The test vehicles were subjected to MSL-3 preconditioning using accelerated conditions of 60° C./60% RH for 40 hours after which the samples were passed through 3× solder reflow with a peak temperature of 260° C. according to JSTD020D-01. They were then subjected to thermal shock test from −55° C. to +125° C., air-to-air, according to JESD22-A104C. Electrical continuity of the daisy chains was checked after reflow and periodically during thermal cycling for assessing the reliability. A total 86 functional daisy chains were fabricated including 47 chains on board #1 and 39 chains on board #2. The testing excluded two daisy chains because of mechanical damage during handling after solder reflow. The measured initial (0-hour) resistance of an entire through-hole daisy chain including 250 holes was less than 1.3 ohms for all the chains except 3 chains, which exhibited much higher resistance indicating process induced defects. Upon analysis of the chains which exhibited much higher initial resistance, it was found that only part of the through-holes in those chains was covered by the landing pads due to misalignment between the landing pads and through holes leading to higher initial resistance. The measured resistance for all through-hole chains includes the contact resistance and the resistance of traces in addition to the resistance of through-holes. During thermal cycling, no significant resistance (10%) change was observed for all the chains with initial resistance less than 1.3 ohms.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

We claim:

1. An embedded integrated circuit (IC) package structure, comprising:
    a substrate having a first side and a second side;
    a dielectric layer disposed on the first side of the substrate, wherein the dielectric layer defines a cavity, the cavity being configured to receive and embed an IC;
    a plurality of through-vias defined within the substrate extending at least from the first side of the substrate to the second side of the substrate and directly below the active IC, wherein the through-vias also act as bonding pads to electrically interconnect the active IC to the second side of the substrate; and
    a metal redistribution layer comprising a plurality of fan-out routing wires disposed on the second side of the substrate configured to interconnect the active IC to a circuit board or to other IC packages.

2. The structure of claim 1, wherein the plurality of through-vias are less than about 150 μm center to center in pitch.

3. The structure of claim 1 wherein the overall thickness of the embedded IC package structure is less than about 250 μm.

4. The structure of claim 1, wherein the active surface of the active IC is on the bottom of the active IC.

5. The structure of claim 1, wherein the active surface of the active IC is on the top of the active IC.

6. The structure of claim 1, wherein the active IC is matched in thickness to the cavity defined within the dielectric layer.

7. The structure of claim 1, wherein the top surface of the IC and the top surface of the cavity are co-planar such that the IC is embedded within the dielectric layer.

8. The structure of claim 1, wherein the substrate is about 30 μm to about 250 μm in thickness.

9. The structure of claim 1, wherein the plurality of through-vias are bumpless.

10. The structure of claim 1, further comprising a plurality of bumps connected to I/O pads on the active surface of the active IC.

11. The structure of claim 10, further comprising bonding pads disposed on the first side of the substrate and aligned with the cavity for electrically interconnecting the plurality of bumps to the through vias.

12. The structure of claim 11, wherein the plurality of bumps are made of copper, solder, tin, other metal alloys, electrically conductive pastes or any combination thereof.

13. The structure of claim 1, wherein the substrate is being made of a polymer-glass composite material, a glass material, a glass-reinforced polymer material, silicon, or combinations thereof.

14. The structure of claim 1, wherein the plurality of through-vias are filled with copper.

15. The structure of claim 1, wherein the plurality of through-vias are filled with copper and an additional metal or alloy.

16. The structure of claim 15, wherein the metal or alloy is selected from a group comprising of tin, tin-silver, tin-copper, tin-silver-copper, or any other metal or alloy with a melting point below about 300° C.

17. The structure of claim 15, wherein the metal or alloy filling the plurality of through-vias is recessed below the surface of the substrate at the base of the cavity.

18. The structure of claim 15, wherein the metal or alloy filling the plurality of through-vias is above the surface of the substrate at the base of the cavity.

19. An embedded integrated circuit (IC) package structure, comprising:
    a substrate having a first side and a second side, the substrate being about 25 to about 250 micrometers in thickness;
    a dielectric layer having a first side and a second side, wherein the second side of the dielectric layer is disposed on the first side of the substrate, and wherein the dielectric layer defines a cavity to receive and embed a first IC;
    a first plurality of through-vias defined within the substrate extending at least from the first side of the substrate to the second side of the substrate and aligned directly below the cavity, wherein the first plurality of through-vias also act as bonding pads to electrically interconnect a plurality of I/O pads disposed on an active surface of the first IC to the second side of the substrate;
    a first metal redistribution layer comprising a plurality of fan-out routing wires disposed on the second side of the substrate configured to interconnect the first IC to a circuit board or to other IC packages;
    a second metal redistribution layer comprising a plurality of fan-out routing wires disposed on the first side of the dielectric layer also configured to interconnect the first IC to additional ICs or to other IC packages; and
    a second plurality of through-vias defined within the substrate and the dielectric layer extending at least from the second side of the substrate to the first side of the dielectric layer to electrically connect a plurality of I/O pads disposed on an active surface of the second IC to the second side of the substrate.

20. The structure of claim 19, wherein the active surface is on the bottom of the first and second ICs.

21. The structure of claim 19, wherein the active surface is on the top of the first and second ICs.

22. The structure of claim 19, wherein the first plurality of through-vias are less than about 150 μm center to center in pitch.

23. The structure of claim 19, wherein the overall thickness of the embedded IC package is less than about 250 μm.

24. The structure of claim 19, wherein the first IC is matched in thickness to the cavity, such that the first IC and the top surface of the cavity are co-planar.

25. The structure of claim 19, further comprising a second IC assembled on the first side of the dielectric layer and electrically connected to the first IC.

26. The structure of claim 19, wherein the plurality of first and second through-vias are bumpless.

* * * * *